United States Patent [19]

Belleville et al.

[11] 4,155,993

[45] May 22, 1979

[54] PROLONGED-RELEASE PHARMACEUTICAL COMPOSITIONS FOR ORAL ADMINISTRATION, THEIR METHODS OF MAKING AND USE

[75] Inventors: Maryse Belleville; Francoise Merle; Jean-Claude Lechevin, all of Lyon, France

[73] Assignee: Lipha, Lyonnaise Industrielle Pharmaceutique, Lyon, France

[21] Appl. No.: 869,238

[22] Filed: Jan. 13, 1978

[30] Foreign Application Priority Data

Jan. 13, 1977 [FR] France .................... 77 00810

[51] Int. Cl.$^2$ .................... A61K 9/36; A61K 9/22
[52] U.S. Cl. .................... 424/35; 424/19
[58] Field of Search .................... 424/35, 19–22

[56] References Cited

U.S. PATENT DOCUMENTS

| | | | |
|---|---|---|---|
| 2,887,440 | 5/1959 | Greminger et al. | 424/35 |
| 3,247,066 | 4/1966 | Milosovich | 424/35 |
| 3,334,096 | 8/1967 | Szarvasi et al. | 260/247.2 |
| 3,388,041 | 6/1968 | Gans et al. | 424/35 |
| 3,538,214 | 11/1970 | Polli et al. | 424/35 |
| 3,835,221 | 9/1974 | Fulborth et al. | 424/35 |
| 3,917,813 | 11/1975 | Pedersen | 424/35 |
| 4,083,949 | 4/1978 | Benedikt | 424/35 |

FOREIGN PATENT DOCUMENTS

| | | | |
|---|---|---|---|
| 1290661 | 3/1962 | France. | |
| 3843M | 2/1966 | France. | |
| 978265 | 12/1964 | United Kingdom | 424/35 |

*Primary Examiner*—Shep K. Rose
*Attorney, Agent, or Firm*—Browdy and Neimark

[57] ABSTRACT

An orally administrable pharmaceutical composition comprises a dosage of the acid oralate of naftidrofuryl having a prolonged release coating which is a film formed from hydroxypropyl methyl cellulose and ethyl cellulose, the content of ethyl cellulose being between 30 and 50% and containing 8 to 15% of propylene glycol relative to the total of the cellulose derivatives.

The composition, having prolonged therapeutic activity is capable of being used in the treatment of arterial diseases in limbs, circulatory disorders in the hands and feet, cerebral vascular disorders and diffuse circulatory insufficiency with elderly people.

3 Claims, No Drawings

PROLONGED-RELEASE PHARMACEUTICAL COMPOSITIONS FOR ORAL ADMINISTRATION, THEIR METHODS OF MAKING AND USE

FIELD OF THE INVENTION

The present invention concerns a pharmaceutical composition for oral administration.

BACKGROUND OF THE INVENTION

Naftidrofuryl (also known as nafronyl), the acid oralate of which is marketed under the trade mark "Praxilene" is known for its action in connection with the treatments of arterial diseases of the limbs, circulatory disorders in the hands and feet, cerebral vascular disorders and the diffuse circulatory insufficiency in connection with elderly people.

In the form of a free base and a salt capable of being used therapeutically, it forms the subject of the U.S. Pat. No. 3,334,096 and French Special Medicament Pat. 3,843 M in the name of the present assignee.

Naftidrofuryl is the compound 3-(1-naphthyl)-2-tetrahydrofurfurylpropionic acid 2-(diethylamino)-ethyl ester and the acid oxalate of this compound (Praxilene) is represented by the formula

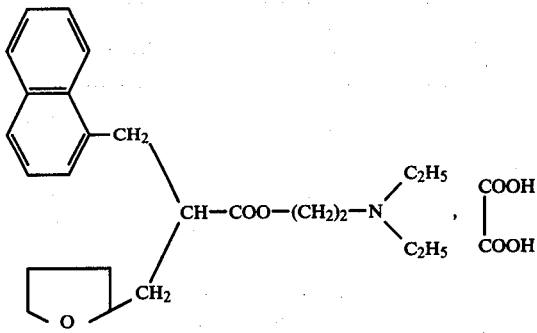

Praxilene is normally available for oral administration in the form of hard gelatine capsules and ampoules. However, such perorally administrable dosage forms give immediate release of the therapeutically active compound.

It is, however very important to prolong the therapeutic activity, thereby assuring an equal and continuous covering, especially of the cerebral circulation, for a complete period of 24 hours. Accordingly, research has been made to find a pharmaceutical preparation of naftidrofuryl, which obviates the disadvantages of a massive arrival of the active principle, followed by a decrease in the therapeutic effect due to the disappearance of the active principle in the circulating fundus. It is necessary to avoid every discontinuity in the cerebral irrigation, particularly during the second part of the night, when the circulation has to be intense. A discontinuity in the effect of the active product would produce the danger of causing a slowing down in the cerebral irrigation and could cause an ischemic cerebral disorder, between the completion of the effect from the first dosage of the medicine and the following dosage.

SUMMARY OF THE INVENTION

A novel preparation of naftidrofuryl with a prolonged therapeutic activity has been found, which is presented as coated tablets. The decrease in the speed of dissolution of the naftidrofuryl from the tablet in the digestive tract, which conditions the prolongation of the therapeutic effect, is obtained by coating the tablet with a dialysis membrane. This membrane is permeable to the digestive juices and permits slow diffusion of the dissolved naftidrofuryl, thus assuring a regular and prolonged absorption. It is expedient to obtain tablets with a sufficient hardness for the coating and with rapid dissolution on contact with digestive juices, in such a way as to obtain a rapid solubilisation of the naftidrofuryl within the coating with use of a dialysis membrane. The nature of the coating film has to be such that the film does not disintegrate on contact with the digestive juices, but presents a sufficient permeability for permitting the passage thereof for dissolving the naftidrofuryl, and then its diffusion.

The coating or covering of the naftidrofuryl tablets is formed by a film which is based on cellulosic polymers, such as cellulose ethers. What is preferably selected is a mixture of hydrophilic compound, such as hydroxypropyl methyl cellulose, and a hydrophobic compound, such as ethyl cellulose.

It has been established that the speed of diffusion of the naftidrofuryl is influenced by the percentage of ethyl cellulose which is used in the mixture of cellulosic polymers; this content may vary, depending on the therapeutic effect which is desired.

On the other hand, the presence in the film-forming solutions of a compound having plasticizing properties, such as propylene glycol, permits the flexibility and the plasticity of the film to be improved. It has in addition been found that the plasticizer, introduced in established proportions, modifies the properties of the dialysis membrane and thus influences the speed at which the naftidrofuryl dissolves.

DETAILED DESCRIPTION OF PREFERRED EMBODIMENTS

The medicinal composition for oral use in accordance with the present invention is a tablet coated with a film of cellulosic polymers formed by a mixture of hydroxypropyl methyl cellulose and ethyl cellulose, containing propylene glycol as plasticizer. This composition is characterized by a content of ethyl cellulose which is between 30 and 50% and an amount of propylene glycol which is between 8 and 15%, expressed as a percentage by weight relative to the total of the cellulosic derivatives. As regards the naftidrofuryl, the preferential content of ethyl cellulose which is used is from 35 to 45% in the mixture of cellulosic polymers, and very advantageously is from 43 to 45%.

The composition of the film-forming solution, particularly the percentage of ethyl cellulose in the mixture of cellulosic polymers, and the quantity of propylene glycol, have to be very carefully established in order to obtain a prolonged therapeutic activity, with the speed of liberation of the naftidrofuryl and the precise therapeutic effect which is required.

The speed of dissolution of the naftidrofuryl is measured in an apparatus which is developed from that described by LEVY, at 37° C. and with gentle agitation (60 rpm), so as to come close to physiological conditions. The testing liquids, prepared from gastric media and artificial intestines, permit a pH gradient from 1.2 to 7.5 to be obtained, this representing the variation in the pH of the gastro-intestinal tract. The dissolved naftidrofuryl is dosed at regular intervals in the test liquid by ultra-violet spectrometry at 283 nm.

The thickness of the coating of the tablet has an influence on the speed at which the naftidrofuryl dissolves, and preferably a coating thickness is selected which corresponds to a dosage of unitary weight which is between 1 and 2%, depending on the desired prolongation of the therapeutic effect.

The verification of the prolongation of the therapeutic effect is carried out in vivo by the comparative measurement of the rates of blood flow obtained in a Beagle dog after administration of a pharmaceutical form of immediate-action naftidrofuryl (hard gelatine capsule) and administration of the prolonged-action pharmaceutical form according to the present invention. The comparison of the times necessary for obtaining the blood flow equal to half of the maximum blood flow likewise serves as a criterion for judging the prolonged effect.

The dosage of the blood naftidrofuryl is erected on the plasma obtained from the venous blood taken from heparin. After extraction in alkaline organic medium and then after passage in acid aqueous medium, the naftidrofuryl is measured out by spectrofluorimetry at 337 nm.

In addition to the verification of the prolongation of the therapeutic effect, the test in vivo showed that the prolonged-action pharmaceutical form according to the invention has a bio-availability which is equal to or even better than that of the immediate-action form.

The tablets of prolonged-action naftidrofuryl are prepared from calibrated granules containing the naftidrofuryl, to which are added conventional excipients: talc and magnesium stearate, so as to obtain, by mixing and compression, tablets which are coated with a film-forming solution constituted by hydroxypropyl methyl cellulose and ethyl cellulose and containing propylene glycol in the proportions indicated by the invention.

The coating of the tablets can be carried into effect by various technical procedures, for example, by centrifuging, and particularly by using a fluidized bed with the film-forming solution.

Several examples which illustrate the invention are given below, simply by way of illustration.

EXAMPLE 1: Preparation of tablets of prolonged-action naftidrofuryl.

6.8 kg of naftidrofuryl are mixed with 0.102 kg of colloidal silica and then with 3.25 kg of lactose. The mixture is wetted with a solution of polyvinyl pyrrolidone in water and isopropanol (0.102 kg) and then passed over a sieve so as to obtain a calibrated granule. After drying, 0.51 kg of talc and 0.136 kg of magnesium stearate are added. After mixing and compression, tablets weighing 320 mg are obtained, which contain 200 mg of naftidrofuryl and dissolving in 30 minutes. The measurement of the speed at which the naftidrofuryl dissolves in artificial medium gives the following results:

| Naftidrofuryl dissolved after | 15' | 50% |
|---|---|---|
| | 30' | 74% |
| | 45' | 99% |

These tablets are coated in a fluidized air bed with the film-forming solution which has the following composition:

| Hydroxypropyl methyl cellulose 65 HG 50 cps | 20 g |
|---|---|
| Ethyl cellulose 20 cps | 15 g |
| Propylene glycol | 3 g |
| Isopropanol | 500 ml |
| Dichloromethane | 500 ml |

After coating, the weight per unit volume of the tablets is increased by about 1.5% and the investigation of the dissolution as a pH gradient leads to the following results:

| Naftidrofuryl dissolved after | 1 hour | 16% |
|---|---|---|
| | 2 hours | 36% |
| | 3 hours | 54% |
| | 4 hours | 72% |
| | 5 hours | 85% |
| | 6 hours | 91% |

EXAMPLE 2: Influence of the percentage of hydrophobic polymer (ethyl cellulose) on the speed at which the naftidrofuryl dissolves.

The tablets prepared according to Example 1 are coated with a film-forming solution having a variable content of ethyl cellulose.

| Percentage of naftidrofuryl dissolved after | Percentage of ethyl cellulose | | | | | |
|---|---|---|---|---|---|---|
| | 33 | 35 | 38 | 43 | 45 | 50 |
| 1 hour | 45 | 35 | 28 | 16 | 11.5 | 2.5 |
| 2 hours | 73 | 66 | 59 | 36 | 30 | 10 |
| 3 hours | 94 | 89 | 80 | 54 | 47 | 22 |
| 4 hours | | 97 | 96 | 72 | 68 | 34 |
| 5 hours | | | | 85 | 84 | 44 |
| 6 hours | | | | 91 | 91 | 55.5 |

EXAMPLE 3: Influence of the plasticizer on the permeability of the film.

The tablets according to Example 1 have been coated with a film-forming solution, in accordance with Example 1, having a variable content of propylene glycol. The investigation of the dissolution as a pH gradient gives the following values:

| Percentage of naftidrofuryl dissolved after | Percentage of propylene glycol | | | |
|---|---|---|---|---|
| | 0 | 2.5 | 8.5 | 15 |
| 1 hour | 2 | 9.5 | 16 | 19 |
| 2 hours | 11 | 28 | 36 | 40 |
| 3 hours | 16.5 | 44 | 54 | 55 |
| 4 hours | | 64 | 72 | 78 |
| 5 hours | 34 | 78 | 85 | 90 |
| 6 hours | 42 | 86 | 91 | 98 |

EXAMPLE 4: Verification of the prolonged effect in vivo.

A Beagle dog, having an empty stomach for 18 hours, has administered thereto a naftidrofuryl tablet according to Example 1, and then, after a rest period, two capsules with 100 mg of naftidrofuryl. The test is repeated four times.

The following table indicates the average time the blood flows, the time necessary for obtaining the maximum blood flow and the mean duration of the maximum half-blood flow for each pharmaceutical form.

|  | 2 capsules, i.e. 200 mg of naftidrofuryl | 1 tablet according to Example 1, i.e. 200 mg of naftidrofuryl |
| --- | --- | --- |
| blood flows in μg/ml at |  |  |
| 30 minutes | 0.22 | 0 |
| 1 hour | 0.81 | 0.18 |
| 2 hours | 0.86 | 0.38 |
| 3 hours | 0.50 | 0.53 |
| 4 hours | 0.22 | 0.70 |
| 5 hours | 0.09 | 0.60 |
| 6 hours | 0.11 | 0.34 |
| 7 hours | 0.02 | 0.26 |
| time necessary for obtaining the maximum blood flow in hours | 2 hours | 4 hours |
| time in hours for the maximum half-blood flow | 2 hrs 30 min. | 4 hours |

The variation in the time which is necessary for obtaining the maximum blood flow and the increase in the duration of the maximum half-blood flow show that the tablet which is prepared in accordance with Example 1 is well equipped for a prolonged activity.

EXAMPLE 5: Bio-availability of the prolonged-effect tablet.

The bio-availability can be appreciated by measurement of the surface under the curve of the blood flow as a function of time, expressed in μg/ml×h, determined in accordance with Example 4. As regards the immediate-action form (hard gelatine capsule), it is 2.46 μg/ml×h. for the tablet according to example 1, it is 2.87 μg/ml×h.

Not only is it that the bio-availability of the naftidrofuryl is not modified, but it appears to be slightly improved.

We claim:

1. An orally-administrable prolonged-release compressed tablet pharmaceutical composition, comprising, as an essential active ingredient, the acid oxalate of 3-(1-naphthyl)-2-tetrahydrofurfurylpropionic acid 2-(diethylamino)-ethyl ester and a prolonged release coating consisting of a film composed of hydroxypropylmethylcellulose and ethyl cellulose, the ethyl cellulose content being in the range of from 30 to 50% by weight, and, as a plasticizer therefore, from 8 to 15 weight percent of propylene glycol, both percentages being based on the total weight of the hydroxypropylmethylcellulose and ethyl cellulose, the thickness of the coating film being such as to increase the weight of the dosage unit by from 1 to 2%.

2. A composition as claimed in claim 1, wherein the ethyl cellulose content is from 35 to 45% by weight and the propylene glycol content is from 8 to 10% by weight.

3. A composition as claimed in claim 1, wherein the ethyl cellulose content is from 43 to 45% by weight and the propylene glycol content is from 8 to 10% by weight.

* * * * *